United States Patent [19]

Weinstock

[11] 4,352,754
[45] Oct. 5, 1982

[54] 3-THIENYLMETHYL-6-HALO-7,8-DIHYDROXY-1-PHENYL-2,3,4,5-TETRAHYDRO-1H-3-BENZAZEPINES

[75] Inventor: Joseph Weinstock, Phoenixville, Pa.

[73] Assignee: SmithKline Corporation, Philadelphia, Pa.

[21] Appl. No.: 158,833

[22] Filed: Jun. 12, 1980

Related U.S. Application Data

[60] Division of Ser. No. 893,238, Apr. 4, 1978, Pat. No. 4,255,422, which is a continuation-in-part of Ser. No. 742,965, Nov. 17, 1976, Pat. No. 4,160,765.

[51] Int. Cl.³ .................... C07D 223/16; A61K 31/55
[52] U.S. Cl. ................................ 260/330.3; 424/275; 260/330.9
[58] Field of Search .................... 260/239 BB, 330.3; 549/59

[56] References Cited

U.S. PATENT DOCUMENTS

| | | | |
|---|---|---|---|
| 3,609,138 | 9/1971 | Mull | 260/239 BB |
| 3,686,167 | 8/1972 | Fujimura et al. | 260/239 BB |
| 4,111,957 | 9/1978 | Holden et al. | 549/59 |
| 4,172,890 | 10/1979 | Holden | 260/330.3 X |
| 4,233,217 | 11/1980 | Shelty | 260/330.3 X |

FOREIGN PATENT DOCUMENTS 555831 2/1967 Switzerland ................ 260/239 BB

*Primary Examiner*—David B. Springer
*Attorney, Agent, or Firm*—William H. Edgerton; Richard D. Foggio; Alan D. Lourie

[57] ABSTRACT

3-Furylmethyl- and thienylmethyl-6-halo-7,8-dihydroxy-1-phenyl-2,3,4,5-tetrahydro-1H-3-benzazepines have potent dopaminergic activity. As such they have utility an antihypertensive and anti-Parkinsonism agents.

5 Claims, No Drawings

3-THIENYLMETHYL-6-HALO-7,8-DIHYDROXY-1-PHENYL-2,3,4,5-TETRAHYDRO-1H-3-BENZAZEPINES

This application is a divisional application of copending Ser. No. 893,238 filed Apr. 4, 1978 and issued on Mar. 10, 1981 as U.S. Pat. No. 4,255,422 which is in turn a continuation-in-part application of Ser. No. 742,965 filed Nov. 17, 1976 which is now U.S. Pat. No. 4,160,765 issued Jul. 10, 1979.

This invention offers a new group of compounds which are 1-phenyl-2,3,4,5-tetrahydro-1H-3-benzazepines having at least three substituents in the benz-ring of the nucleus, one of which is a halo or halo-containing group substituted at the 6-position and the other two, 7,8-dihydroxy groups. These dopamine agonists have utility as medicinally active compounds especially as cardiovascular and/or diuretic agents due in part to their peripheral dopaminergic activity or as anti-Parkinsonism agents by means of activity at the central dopamine receptors. Generally speaking therefore they have either potent peripheral or central dopaminergic activity.

STATEMENT OF THE PRIOR ART

Certain 1-phenyl-2,3,4,5-tetrahydro-1H-3-benzazepines have been described in U.S. Pat. Nos. 3,393,192, 3,609,138, 3,743,731, 4,052,506 and 4,011,319; British Pat. No. 1,118,688; and Swiss Pat. No. 555,831, including general methods of preparation. However these references disclose no specific benz- trisubstituted compounds, no 6-halo-substituted compounds of any kind and no particular advantage to 6-halo substitution in the structures. British Pat. No. 1,225,053 discloses certain halo-substituted benzazepines not related in structure to those claimed here.

DISCLOSURE OF THE INVENTION

The structures of the compounds of this invention are specifically identified by having a halo, that is, a chloro, bromo, iodo or fluoro or halo-containing substituent such as a trifluoromethyl or trifluoro ethyl group at the 6-position of the 7,8-dihydroxy-1-phenyltetrahydro-1H-3-benzazepine system. Exemplary of this new group of compounds are those represented by the following structural formulas:

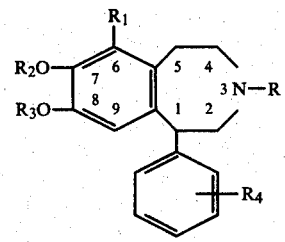

in which:

R is hydrogen, furylmethyl or thienylmethyl;

$R_1$ is halo, especially chloro, fluoro or bromo, or trifluoromethyl;

$R_2$ and $R_3$ are each hydrogen or a group derived therefrom such as lower alkanoyl of 2-7 carbons for example acetyl, propionyl, isobutyryl, valeryl etc; and $R_4$ is hydrogen or from 1 to 3 common phenyl substituents such as trifluoromethyl, halo such as chloro, fluoro or bromo, methyl, methoxy or when substituted with another substituent other than hydrogen, hydroxy or acetoxy.

$R_2O$ and $R_3O$ are preferably hydroxy radicals at the 7,8 positions for maximal biological activity.

A subgeneric group of compounds within the above illustrative generic group are those of Formula I in which R is hydrogen; $R_2$ and $R_3$ are the same and are hydrogen, isobutyryl or acetyl; and $R_4$ is hydrogen.

Individual compounds of note are those of Formula II

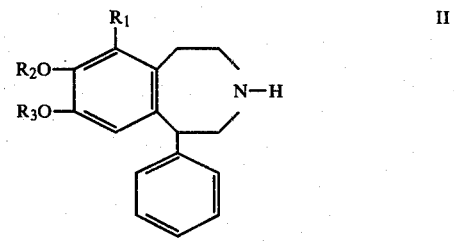

in which $R_1$ is chloro or bromo and $R_2$ and $R_3$ are the same and are hydrogen or acetyl.

The pharmaceutically acceptable acid addition salts having the utility of the free bases of formula I, prepared by methods well known to the art, are formed with both inorganic or organic acids, for example: maleic, fumaric, benzoic, ascorbic, pamoic, succinic, bis-methylenesalicylic, methanesulfonic ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phsophoric and nitric acids. The hydrohalides or methane sulfonates are preferred.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Specific methods of resolution are disclosed in Swiss Pat. No. 555,831. Unless otherwise specified herein or in the claims, it is intended to include all isomers, whether separated or mixtures thereof. Where isomers are separated, the desired pharmacological activity will usually predominate in one of the isomers.

The compounds of Formula I in which R is hydrogen are generally prepared from intermediates of the following formula:

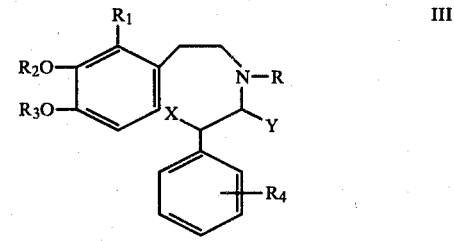

in which X is hydroxyl or its functional equivalent, Y is $H_2$ or $=O$, R is hydrogen or a chemically inert substituent as defined above, $R_1$ is halo or trifluoromethyl; $R_2$ and $R_3$ are lower alkyl benzyl or together are methylene or ethylene; and $R_4$ is hydrogen or one or more chemically inert substituents of the group described above, by means of an intramolecular cyclization effected by reaction with a cyclizing agent such as a strong acid for example sulfuric acid, the preferred sulfuric acid in trifluoroacetic acid, polyphosphoric acid, polyphosphoric ester, methanesulfonic acid in methylene chloride or hydrobromic acid or a Lewis acid such as boron trifluoride, aluminum chloride or stannic chloride which generates the desired carbonium ion from the substituent X. The term "chemically inert" means under the conditions of the cyclization reaction the substituent is not altered unless of course the operator so desires. For example carrying out the cyclization in 48% hydrobromic acid when $R_2$ or $R_3$ are methyl splits the ether links to give the desired hydroxy cyclic compounds.

The phenethylamines (IV) which are used as starting materials for this method are either known or are prepared by methods described in U.S. Pat. No. 3,211,792, Chem. Abst. 80,95398, U.S. Pat. No. 3,869,474, U.S. Pat. No. 3,804,839, J. Am. Chem. Soc., 78, 4419 (1956) or in the illustrative examples here disclosed.

Alternatively, the compounds of Formula I especially where R is hydrogen may be prepared from 1-phenyl-2-oxo-2,3,4,5-tetrahydro-1H-3-benzazepine intermediates which are obtained by heating an appropriate phenylalkylamine with an ester of mandelic acid to give the amide of Formula III where Y is =O. The latter is then cyclized as described above to from the 2-oxobenzazepine intermediates which are chemically reduced by standard amide reducing agents, for example with borane, diborane, lithium aluminum hydride, sodium borohydride and propionic acid, diisobutyl aluminum hydride or sodium bis (2-methoxyethoxy) aluminum hydride, to the 1-phenyl-3-benzazepine products.

The compounds in which $R_1$ is bromo and $R_2$, $R_3$, $R_4$ and R contain only chemically inert groups can surprisingly be prepared by direct bromination at the 6-position of their chemical structures in excellent yields. This reaction is carried out most conveniently using about two mole equivalents of bromine in a suitable solvent such as acetic acid at about room or ambient temperature. The yield of the product in which $R_1$ is bromo, $R_2O$— and $R_3O$— are 7,8-dimethoxy and R and $R_1$ are hydrogen is 70–85%. The product separates from the bormination mixture as a complex with one mole of bromine. The complexed bromine is eliminated easily by treatment with methanol/acetone.

The 6-bromo containing compound may optionally serve as an intermediate in a number of ways such as for preparing the 6-chloro, trifluoromethyl or iodo congeners. The 6-bromo compound is also useful for preparing 6-lithium or Grignard intermediates. These can be reacted with a number of conventional reactants to introduce 6-substituents such as with iodine, halogenating agents, i.e. hexachloroethane, chlorine, N-chlorosuccinimide and others to introduce halo substituents. In effect this is a halogen halogen interchange via a metal substituent. The lithium salts and bromination process are part of this invention claimed elsewhere.

To prepare the compounds of Formula I where $R_1$ or $R_2$ is alkanoyl, the corresponding 3-benzyl-dihydroxy-3-benzazepine (obtained by N-alkylation of the hydroxybenzazepine with benzyl bromide in the presence of potassium carbonate) is treated with the appropriate alkanoic acid anhydride or chloride, for example acetic anhydride, and the resulting alkanoyloxy substituted benzazepine is then hydrogenated in the presence of palladium-on-carbon to remove the protective benzyl group. The dialkanoyloxy derivatives such as the important 7,8-diacetoxy compounds can also be prepared by direct O-acylation of the 7-halo-7,8-dihydroxy-1-phenyl-2,3,4,5 tetrahydro-1H-3-benzazepine hydrobromide in trifluoroacetic acid at ambient temperature with the anhydride or halide.

The intermediates of Formula III above are conveniently prepared by heating equimolar amounts of a styrene oxide with a 2-halo-3,4-dialkoxyphenethylamine which is either known or prepared by methods known to the art, each appropriately substituted, either alone or in an inert organic solvent such as tetrahydrofuran. Preferably the heating is effected on a steam bath or at reflux temperature for from 12 to 24 hours. The required styrene oxide is conveniently prepared by reaction of the ylide derivative from sodium hydride and trimethylsulfonium iodide with the appropriately substituted benzaldehyde.

Alternatively the phenethanolamine intermediates are prepared by condensing the 2-halo-3,4-dialkoxy-phenethylamines with a blocked or hindered phenyl-halohydrin such as:

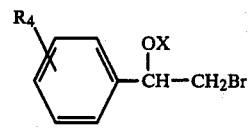

in which X is a blocking group known to the art such as tert. butyl.

The active dopaminergic compounds of this invention which stimulate peripheral dopamine receptors, for example, increase renal blood flow and have as an end result antihypertensive activity. This renal vasodilator activity of the benzazepine compounds of Formula I is conveniently measured in an anesthetized dog (see U.S. Pat. No. 4,011,319). In this pharmacological procedure, a test compound is administered at progressively increasing (3-fold) infusion rates beginning at 0.1 mcg/kg/min up to 810 mcg/kg/min for 5 minutes each to anesthetized normotensive dogs and the following parameters are measured: renal artery blood flow, iliac artery blood flow, arterial blood pressure and heart rate. Results are reported as a percent change, increase or decrease, at time of peak response (from pre-drug controls), and for a significant effect renal blood flow (increase) and renal vascular resistance (decrease) should be approximately 10% or greater. The effect on renal vascular resistance can be calculated from any change in renal blood flow and arterial blood pressure. To confirm the mechanism of action, representative active renal vasodilator compounds are checked for blockade by bulbocapnine which is known to be a specific blocker of renal dopamine receptors. Representative advantageous compounds of Formula I, 7,8-dihydroxy-1-phenyl-2,3,4,5-tetrahydro-1H-3-benzazepine substituted at the 6-position by chloro or bromo, tested by i.v. infusion as described above produced an $ED_{15}$ of 3.5 and 22 (9) mcg/kg respectively with little direct effect on systemic blood pressure in normotensive animals. $ED_{15}$ therefore is the cumulative dose by infusion which produces a 15% decrease in renal vascular resistance ($R=B.P.$ in mm/hg/$B.F.$ ml/min). As a renal vasodilator in the anesthetized dog this 6-chloro compound was 10 times more efficacious than its 6-deschloro congener.

The compounds of this invention unexpectedly also cause a separation of side effects in dogs such as those caused by pressor reactions due to norepinephrine compared with the $ED_{15}$ cardiovascular dose as described above. Here the above 6-chloro and 6-bromo-7,8-dihydroxy compounds have a separation ratio of 1233 and >1388 respectively compared with their deshalo congener (47).

In addition to the renal vasodilator activity via a dopaminergic effect, certain benzazepine compounds of Formula I produce weak diuretic activity. Such diuretic activity is measured in the standard saline-loaded rat procedure. A test compound is administered i.p. at doses of from 10 to 40 mg/kg and the parameters measured are urine volume (hourly for three hours) plus sodium and potassium ion concentrations. Also conventional diuretic tests in the dog may be used. 6-Chloro-7,8-dihydroxy-1-phenyl-2,3,4,5-tetrahydro-1H-3-benzazepine tested in the phosphate mannitol dog produced a significant increase in renal plasma flow and natriuresis at a dose as low as 5 and 10 micrograms, μg/kg/min i.v. Similar results were obtained at oral doses of 10 mg/kg (renal blood flow only). The 6-chloro-7,8-diacetoxy congener has better activity after oral absorption than does its 7,8-dihydroxy parent.

The benzazepine compounds of Formula I also may have antiparkinsonism activity due to central dopaminergic activity. This CNS activity of course is only possible if the compound crosses the blood-brain barrier following peripheral administration and is thus available at the central dopamine receptor sites. Such central activity is demonstrated by employing a modified standard animal pharmacological test procedure reported by Ungerstedt et al., in *Brain Research* 24, 1970, 485–493. This procedure (see U.S. Pat. No. 4,052,506) is base on a drug induced rotation of rats having extensive unilateral lesions of the substantia nigra. Briefly, the test comprises the quantitative recording of rotational behavior in rats in which 6-hydroxydopamine lesions of the nigrostriatal dopamine system have been produced. A unilateral brain lesion in the left substantia nigra causes the dopamine receptor in the left caudate to become hypersensitive following the resulting degeneration of the nigral cell bodies. These lesions destroy the source of the neurotransmitter dopamine in the caudate but leave the caudate cell bodies and their dopamine receptors intact. Activation of these receptors by drugs which produce contralateral rotation, with respect to the lesioned side of the brain, is used as a measure of central dopaminergic activity of the drug.

Compounds which are known to be clinically effective in controlling parkinsonism, such as, for example, L-dopa and apomorphine, are also effective in this rat turning model. These compounds directly activate the dopamine receptors and cause contralateral rotation of the lesioned rat.

Rotational activity is defined as the ability of a compound to produce 500 contralateral rotations during a two-hour period after administration, usually intraperitoneally. The dose corresponding to 500 contralateral rotations per two hours is obtained and assigned as the $RD_{500}$ value.

Once again advantageous compounds of Formula I, 7-chloro or 7-bromo-7,8-dihydroxy-1-phenyl-2,3,4,5-tetrahydro-1H-3benzazepines when tested as described above in rats produced $ED_{500}$, i.p. of 0.3 and 0.27 mg/kg respectively. Further the compounds do not induce emesis or stereotyped behavior at doses which are effective in the rat turning model.

The same 6-bromo compound showed greater renal plasma flow (RPF) in the rat renal clearance test than did the desbromo congener. At 15 μg/kg/min the RPF increased 60% over control with a 85% increase in urine volume. The 6-chloro compound also increased volume 80%, RPF 48% and sodium ion excretion. Therefore these compounds demonstrate stronger diuretic properties than does their 6-hydrogen congener.

As mentioned above the 6-halo substitutents but not especially the 6-trifluoromethyl substituent unexpectedly increase the potency of the dopaminergic activity of each respective deshalo compound of the prior art. Such an increase in potency is important in reducing the cost of medication or in decreasing the side effect liability of the compound which may be present at higher doses. Following is a tabular compilation of the results of testing, in the two basic screening models for peripheral ($ED_{15}$) or central ($RD_{500}$) dopaminergic activity, selected basic compounds of the series claimed here compared with the compounds having the closest structure in the prior art or with compounds having structures even closer to those claimed. It should be emphasized that we have much more biological data than that presented here but that the following data was selected to demonstrate the unexpected biological activity due to the specific 6-halo-7,8-hydroxy substitution system in the 1-phenyl-2,3,4,5-tetrahydro-1H-3-benzazepine series:

TABLE I

| No. | Salt | R | $R_1$ | $R_2$ | $R_3$ | $R_4$ | $ED_{15}$* | $RD_{500}$** |
|-----|------|---|-------|-------|-------|-------|------------|--------------|
| 1.  | HBr  | H | H     | H     | H     | H     | 80 (3)     | —            |
|     |      |   |       |       |       |       | 35 (3)     | —            |
|     | HCl  | H | H     | H     | H     | H     | 31 (3)     | 0.22         |
| 2.  | HBr  | H | OH    | H     | H     | H     | ina. (2)   | ina.         |
| 3.  | HCl  | H | 9-Cl  | H     | H     | H     | ina. (1)   | 10 (547 ± 215) |
| 4.  | HBr  | H | Cl    | 9-OH  | H     | H     | 4500(2)    | ina.         |
| 5.  | HBr  | H | Cl    | H     | H     | H     | 3.5 (2)    | 0.3          |
| 6.  | HBr  | H | Br    | H     | H     | H     | 9 (3)      | 0.27         |
| 7.  | HBr  | H | F     | H     | H     | H     | 9 (3)      | 4.9 (p.o.)   |

*$ED_{15}$ in mcg/kg. i.v.; with the number of dogs in the test.
**$RD_{500}$ mg/kg. i.p.; if an $RD_{500}$ was not obtained the number of rotations and deviation at a certain dose are present unless the figure is insignificant.

From this data, it is evident that compounds 5–7 have 4 to 10 times the $ED_{15}$ of the closest prior art compound described as a dopaminergic agent (compound 1). Also moving the halo to position 9 (compound 3) reduces the dopaminergic activity almost to nil as does moving the 7-hydroxy group to position 9 (compound 4). Both of these compounds (compounds 3 and 4) are position isomers of those claimed here.

The pharmaceutical compositions of this invention having dopaminergic activity are prepared in conventional dosage unit forms by incorporating a compound of Formula I, an isomer or a pharmaceutically acceptable acid addition salt thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 15 mg to about 100 mg of active ingredient per dosage unit but this quantity depends on the specific biological activity desired and the conditions of the patient. Generally speaking lower doses are needed to stimulate central dopamine receptors than peripheral receptors.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax.

A wide variety of pharmaceutical forms can be employed. Thus, if a solid carrier for oral administration is used the preparation can be tableted, placed in a hard gelatin capsule in powder or pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses will be administered several times such as 2-5 times a day with the daily dosage regimen being selected from about 50 mg to about 2 g. When the method described above is carried out hypotensive, diuretic or antiparkinsonism activity is produced with a minimum of side effects. The O-diacyl derivatives may owe their activity to the parent dihydroxy compound following metabolism in the body. Therefore any compound derived from those of Formula I which owe activity to a parent compound or one of its metabolites is considered a part of this invention.

The following examples are designed solely to illustrate the preparation and use of the compounds of this invention. The temperatures are Centigrade. Other variations of these examples will be obvious to those skilled in the art.

EXAMPLE 1

A mixture of 100 g (0.55 mol) of 3,4-dimethoxyphenylethylamine and 66.2 g (0.55 mol) of styrene oxide in 200 ml of tetrahydrofuran was refluxed overnight. The solvent was removed in vacuo. About 500 ml of n-butyl chloride was added to the residue and the mixture cooled slightly. Filtration furnished N-[2-(3,4-dimethoxyphenyl)ethyl]-2-phenyl-2-hydroxyethylamine, m.p. 92°–93°.

The above prepared phenethylamine, 71.5 g (0.238 mol), was dissolved in 400 ml of acetic acid and the solution was cooled. To this solution was added 16.9 g (0.238 mol) of chlorine gas over a 30 to 45 minute period. The reaction mixture was poured into water, made basic with 40% sodium hydroxide solution and about 250 ml of ether added to the stirred solution. The resulting solid was filtered to give N-[2-(2-chloro-4,5-dimethoxyphenyl)ethyl]-2-phenyl-2-hydroxyethylamine, m.p. 110°–113°.

To 100 ml of concentrated sulfuric acid was added the above phenethylamine (10 g, 30 mmol) with stirring. After about 20 minutes the reaction mixture was poured over ice and extracted with ethyl acetate. The aqueous solution was made basic with sodium hydroxide pellets and 40% sodium hydroxide solution. The oil which forms was extracted with ether, the extract was dried and concentrated to about one-half volume. Ethereal hydrogen chloride was added to furnish 6-chloro-8,9-dimethoxy-1-phenyl-2,3,4,5-tetrahydro-1H-benzazepine hydrochloride, m.p. 209°–210°.

Heating the dimethoxy compound in an excess of 48% hydrobromic acid at reflux for 2 hours and cooling gives the 8,9-dihydroxy congener as the hydrobromide.

EXAMPLE 2

Isovanillin (200 g, 1.32 mole) was suspended in 1200 cc chloroform. Chlorine (103 g, 1.45 mole) was added by means of 3 500 cc portions of carbon tetrachloride, in which it was dissolved. The suspension was stirred vigorously during the addition and the reaction was kept around 25° by a water bath. The suspension was stirred for 22 minutes after the completion of the addition of chlorine. The precipitate was filtered and crystallized from methanol, then recrystallized from isopropanol/ethyl acetate. Yield 98.7 g (40%, m.p. 204°–206°) of 2-chloro-3-hydroxy-4-methoxybenzaldehyde.

The aldehyde product (189.3 g, 1.02 mole) was suspended in 1 l. of dry dimethylformamide, 350 g of potassium carbonate was added. 145 cc (124 g, 1.54 mole) of dimethyl sulfate was added dropwise over a 20 minute period. After the addition the reaction was heated on the steam bath for 5 minutes. 70 cc of water were added and the reaction was again heated for 5 minutes on the steam bath. The mixture was then poured into ice water and the precipitate was collected. It was crystallized from acetic acid/water (800 cc-50 cc). A second crop was obtained from the mother liquor. Yield 180 g (90%) of 2-chloro-3,4-dimethoxybenzaldehyde after drying, m.p. 69°–70°.

The dimethoxybenzaldehyde (180 g. 0.9 mole) was dissolved in 500 cc warm acetic acid. 61 g (0.8 mole) of ammonium acetate was added, followed by 160 cc of nitromethane. The reaction was heated vigorously on the steam bath for 3 hours. Water was then added to the cloud point, while still heating, and the solution was cooled and scratched. The β-nitrostyrene began to oil out and then crystallized. The solution was cooled. The yellow crystals were collected and dried in a vacuum oven. Yield 175 g (80% m.p. 88°–91°) of 2-chloro-3,4-dimethoxy-β-nitrostyrene.

The nitrostyrene (80 g, 0.33 mole) was dissolved in 800 cc of dry tetrahydrofuran. Lithium aluminum hydride, as a 3.7 M solution (260 cc, 0.36 mole), was put in a 5 l. 3 neck flask which has been dried and flushed with argon. It was diluted with 500 cc of dry ether. The solution of the nitrostyrene was added in a thin stream. The flask was cooled in an ice bath so that the heat of reaction caused a gentle reflux of the ether. After addition, the reaction was refluxed one hour, then worked up by adding 36 cc of water, 36 cc of 10% sodium hydroxide and 108 cc of water sequentially and carefully, while cooling the reaction in ice.

The precipitate was collected, washed well with ethyl ether and discarded. The ether-tetrahydrofuran mixture was evaporated.

The above reaction was repeated on 83 g of nitrostyrene. The two crude products were combined and distilled at 0.5 mm to collect at 142°–155° the product containing fraction which was pure 2-(2-chloro-3,4-dimethoxyphenyl)ethylamine by t.l.c. (80 g).

The phenethylamine (25.7 g, 0.12 mole) was heated to 115° in an oil bath. Styrene oxide (14.4 g, 0.12 mole) was added and the reaction was heated for 1 hour. After cooling to ~30°, 2:1 petroleum ether/acetone was added to dissolve the oil; N-[(2-hydroxy-2-phenylethyl)]-N-[2-(2'-chloro-3', 4'-dimethoxyphenyl)ethyl]amine, crystallized out in 37% yield (15 g) m.p. 100°–101°.

The hydroxyphenethylamine (15 g, (0.445 mole) was dissolved in 60 cc of trifluoroacetic acid and 4.05 cc of concentrated sulfuric acid was added. The reaction was refluxed 2 hours. After cooling most of the trifluoroacetic acid was stripped off and the residue was poured into water. It was made basic with 10% sodium hydroxide and was extracted with ether twice. The ether was dried, and as it was evaporated, a solid separated which was collected; m.p. 115°–121°, 6.0 g of 6-chloro-7,8-dimethoxy-1-phenyl-2,3,4,5-tetrahydro-1H-3-benzazepine. The remaining ether was treated with ethereal hydrogen chloride and the hydrochloride salt precipitated; yield 3.2 g, total 62% m.p. 234°–236°. The dimethoxy derivative was converted to 6-chloro-7,8-dihydroxy-1-phenyl-2,3,4,5-tetrahydro-1H-3-benzazepine hydrobromide using boron tribromide in a 77% yield, m.p. 259°–260°.

EXAMPLE 3

7,8-Dimethoxy-1-phenyl-2,3,4,5-tetrahydro-1H-3-benzazepine (280 g, 0.75 mole) was dissolved in 1700 cc of acetic acid. Bromine (280 g, 1.75 mole) was added in a thin stream. The reaction was stirred for two hours. The precipitate, which formed after 1 hour, was collected and washed with ether. It was dissolved in boiling methanol and acetone was added to destroy the bromine excess. 6-Bromo-7,8-dimethoxy-1-phenyl-2,3,4,5-tetrahydro-1H-3-benzazepine hydrobromide was allowed to crystallize from the methanol and a second crop was obtained by adding ether to the mother liquor. Yield 298 g, 77% m.p. 236–238%. This bromination may be applied to any 7,8-dialkoxy or alkanoyloxybenzazepine having a free 6-position.

The hydrobromide was shaken in a mixture of excess 10% sodium hydroxide and methylene chloride. The organic layer was separated, dried and evaporated to give a solid base which was crystallized from toluene-hexane; m.p. 125°–128°, yield 238 g (97%).

The base (12 g, 0.033 mole) was dissolved in 200 cc of methylene chloride and was cooled to −15° C. Boron tribromide (15.4 cc, 16 mole) was added cautiously. The reaction was allowed to run at room temperature for two hours. The solvent was stripped off and the flask was cooled to −15°. Dry methanol was added to destroy the boron tribromide complexes. It was then stripped off. The residue was crystallized from water, then boiled in acetonitrile to aid in the drying of the compound. Yield of 6-bromo-7,8-dihydroxy-1-phenyl-2,3,4,5-tetrahydro-1H-3-benzazepine hydrobromide; 10.26 g (75%), m.p. 240°–242° after vacuum drying.

Other compounds having a free 6-position and no interfering groups such as unsaturated or aromatic activating centers as known to the art may be similarly brominated.

EXAMPLE 4

6-Bromo-7,8-dimethoxy-1-phenyltetrahydrobenzazepine (13 g, 0.0355 mole) was dissolved in 200 cc of dry acetone. Anhydrous potassium carbonate (10 g, 0.07 mole) was added, followed by 4.2 cc (0.0355 mole) of benzyl bromide. The reaction was refluxed four hours. After cooling, the solid was filtered and the filtrate was stripped off. The resulting oil was dissolved in ether, filtered, and ethereal hydrogen chloride was added. The crystalline precipitate of N-benzyl derivative was filtered and recrystallized from methanolether, m.p. 160°–165°.

The solid was then dissolved in methylene chloride and was extracted twice with excess 10% sodium hydroxide. The solvent was dried and evaporated. The residue was dissolved in dry benzene and the benzene was distilled to azeotrope any water present. After repeating the procedure, the oil was pumped under vacuum to remove the benzene. Yield of N-benzyl-6-bromo-7,8-dimethoxy-1-phenyl-2,3,4,5-tetrahydro-1H-3-benzazepine, 12.5 g, 80%.

The 6-bromobenzyl derivative (12.5 g, 0.0277 mole) was converted to its 6-lithium salt which is an important intermediate by reaction with n-butyl lithium in ether. The n-butyl lithium (29 cc, 2.2 M, 0.064 mole) was added via syringe to a 3 neck flask in an organ atmosphere. It was diluted with 3 or 4 volumes of dry ether and cooled to −78° in a dry ice-propanol bath. The benzyl compound was added in 75 cc of dry ether in a thin stream, over a five minute period. The reaction stirred at −78° for five minutes and then 13 g (0.0554 mole) of hexachloroethane was added in 75 cc of ether. The precipitate dissolved immediately.

The reaction mixture was poured into water and the ether layer was retained. The water was extracted again with ether and the ether was dried with magnesium sulfate. Addition of ethereal hydrogen chloride gave a precipitate which was crystallized first from ether-methanol, then from ethyl acetate. Yield of 3-benzyl-6-chloro-7,8-dimethoxy-1-phenyl-2,3,4,5-tetrahydro-1H-3-benzazepine hydrochloride, 9.4 g (80%), m.p. 201°–205°.

This N-benzyl compound (5.33 g, 0.013 mole) was freed from its hydrochloride by extraction into methylene chloride after making alkaline a solution of the hydrochloride. The methylene chloride was dried, evaporated, and the residue dissolved in benzene. It was stripped down to azeotrope any water remaining and the residue was dissolved in 50 cc of dry benzene.

Cyanogen bromide (1.53 g, 0.0144 mole) was dissolved in 50 cc of dry benzene and was warmed to 55°. The N-benzyl compound was added dropwise in benzene and the mixture stirred for 3 hours. The volatiles were stripped off, leaving a solid which was triturated with ether. Yield of N-cyano derivative; 4.0 g (89%), m.p. 149°–151°.

This material (4.0 g, 0.127 mole) was dissolved in a solution of 55 cc of acetic acid, 6 cc of conc. hydrochloric acid and 31 cc of water. It was heated overnight on the steam bath. The solvents were then stripped off and the residue dissolved in hot methanol. Ether was added and 6-chloro-7,8-dimethoxy-1-phenyl-2,3,4,5-tetrahydro-1H-3-benzazepine hydrochloride crystallized; yield 3.85 g (90%), m.p. 241°–245°.

EXAMPLE 5

The product of Example 4 (3.27 g, 0.0103 mole) was freed from its hydrochloride by making basic its aqueous solution and extracting the mixture with methylene chloride. The solvent was carefully dried and cooled to −15° by a methanol-ice bath. Boron tribromide (4 cc) was added and the reaction was stirred at room temperature for 2 hours. The solvent and excess tribromide were stripped and the flask cooled to −78°. Methanol was added cautiously until all the material was dissolved. The methanol was stripped off and the residue crystallized from hot water. The crystals were boiled in dry acetonitrile for an hour, then collected to give 6-chloro-7,8-dihydroxy-1-phenyl-2,3,4,5-tetrahydro-1H-3-benzazepine hydrobromide; (56%), m.p. 256°–260°.

EXAMPLE 6

2-Chloro-3,4-dimethoxyphenethylamine (1.0 g) was reacted with 0.70 g of o-methylstyrene oxide as described above to give the hydroxyphenethylamine. This compound (2.16 g) was stirred at room temperature in 15 ml of trifluoroacetic acid with 4 drops of conc. sulfuric acid. Working up as above gave, after purification over a silica gel column with chloroform, 10% methanol/chloroform as eluates, the desired 6-chloro-7,8-dimethoxy-1-o-methylphenyl-2,3,4,5-tetrahydro-1H-3-benzazepine. This after demethylation gave the 6-chloro-o-methylphenyl, m.p. 233°–236° (HBr salt).

EXAMPLE 7

A mixture of 42.0 g of 57% sodium hydroxide dispersed in oil and 700 ml of dimethyl sulfoxide is stirred at 70°–75° for one to one and one-half hours. The solution is diluted with 700 ml of dry tetrahydrofuran and cooled to 0°, under nitrogen. A 200 g of (1.0 mol) sample of trimethylsulfonium iodide is added in portions, maintaining the temperature between 0°–5°. The mixture is stirred for 15 minutes and then a solution of 70.4 g (0.50 mol) of o-chlorobenzaldehyde in 300 ml of dry tetrahydrofuran is added dropwise. The resulting mixture is stirred at room temperature for four hours, poured into water and extracted with ether. The extract is washed with brine, dried and evaporated in vacuo to leave o-chlorostyrene oxide.

A solution of 27.5 g of N-benzyl-2-chloro-3,4-dimethoxyphenylethylamine and 23.3 g (0.15 mol) of m-chlorostyrene oxide in 50 ml of methanol is stirred and refluxed overnight. The methanol is removed in vacuo and the residual N-benzyl-N-[2-(2-chloro-3,4-dimethoxyphenyl)ethyl]-2-hydroxy-2-(2-chlorophenyl)ethylamine is reduced without further purification. This sample (0.01mol) is dissolved in ether, acidifed with ethereal hydrogen chloride and the hydrochloride precipitates. The latter is dissolved in 90 ml of methanol, the solution is added to a mixture of 0.5 g of palladium-on-charcoal in 10 ml of ethyl acetate and the mixture is hydrogenated at room temperature for 90 minutes at 60 psi. The reaction mixture is filtered and the filtrate evaporated in vacuo to yield N-[2-(2-chloro-3,4-dimethoxyphenyl)ethyl]-2-hydroxy-2-(2-chlorophenyl)ethylamine hydrochloride.

A solution of 6.0 g (0.0161 mol) of the above prepared compound in 250 ml of 48% hydrobromic acid is stirred and refluxed for three hours. The reaction mixture is evaporated in vacuo to give 6-chloro-1-(2-chlorophenyl)-7,8-dihydroxy-2,3,4,5-tetrahydro-1H-3-benzazepine hydrobromide.

EXAMPLE 8

Following the procedure of Example 7 and employing 42.0 g of 57% of sodium hydride in mineral oil, 200 g (0.1 mol) of trimethylsulfonium iodide and 70.4 g (0.50 mol) of o-bromo-benzaldehyde there is obtained o-bromostyrene oxide.

Similarly 2.71 g of N-benzyl-2-chloro-3,4-dimethoxyphenethylamine and 2.33 g (0.015 mol) of o-bromostyrene oxide are reacted in methanol to give N-benzyl-N-[2-(2-chloro-3,4-dimethoxyphenyl)ethyl]-2-hydroxy-2-(2-bromophenyl)ethylamine. The latter is converted to its hydrochloride, which is dissolved in 90 ml of methanol and hydrogenated over 1 g of 10% palladium-on-carbon in 10 ml of ethyl acetate at room temperature for six hours. The reaction mixture is filtered and evaporated in vacuo to leave N-[2-(2-chloro-3,4-dimethoxyphenyl)ethyl]-2-hydroxy-2-(2-bromophenyl)ethylamine hydrochloride.

A solution of 4.0 g of the above hydrochloride in 250 ml of 48% hydrobromic acid is stirred and refluxed for two hours. The reaction mixture is evaporated in vacuo to yield 6-chloro-1-(2-bromophenyl)-7,8-dihydroxy-2,3,4,5-tetrahydro-1H-3-benzazepine hydrobromide.

Substituting trifluoromethyl, fluoro, methyl, ethyl, ethoxystyrene oxides will give the compounds of this invention whose structures include the corresponding substituted 1-phenyl moieties.

EXAMPLE 9

4.0 g sample of 3-benzyl-6-chloro-7,8-dihydroxy-1-phenyl-2,3,4,5-tetrahydro-1H-3-benzazepine (prepared from the 3-unsubstituted benzazepine by reaction with benzyl bromide in the presence of potassium carbonate) is dissolved in 50 ml of acetic anhydride and the solution is heated on a steam bath for one hour. The reaction mixture is cooled, ice-water is added and the solution is evaporated to dryness. The residue is triturated with ethyl acetate, the solution washed with water, dried and the solvent removed in vacuo to leave an oil. The latter is dissolved in ether and ethereal hydrogen chloride is added to precipitate 3-benzyl-6-chloro-7,8-diacetoxy-1-phenyl-2,3,4,5-tetrahydro-1H-3-benzazepine hydrochloride.

The diacetoxy compound prepared above, 3.5 g is dissolved in 100 ml of ethanol and 1 g of 10% palladium-on-carbon is added. The mixture is hydrogenated in a Parr apparatus at 50° under 50 psi of hydrogen for one hour. The reaction mixture is filtered and the filtrate was evaporated to give 6-chloro-7,8-diacetoxy-1-phenyl-2,3,4,5-tetrahydro-1H-3-benzazepine hydrochloride. This compound has a melting point of 234°–235°.

Alternatively 6-chloro-7,8-dihydroxy-1-phenyl-2,3,4,5-tetrahydro-1H-3-benzazepine hydrobromide (10 g) is dissolved in trifluoroacetic acid and reacted with a stoichiometric amount of acetyl chloride at room temperature. The next day the reaction mixture is evaporated and the residue recrystallized to give the desired diacetoxy derivative.

Substituting other alkanoyl anhydrides or chlorides gives various 7,8-alkanoyl derivatives.

EXAMPLE 10

Substituting a stoichiometric quantity of 2-fluoro3,4-dimethoxyphenethyl amine in the synthetic procedures above gives 6-fluoro-7,8-dimethoxy-1-phenyl-2,3,4,5-tetrahydro-1H-3-benzazepine. Hydrolysis with boron tribromide as in Example 2 gives 6-fluoro-7,8-dihydroxy-1-phenyl-2,3,4,5-tetrahydro-1H-3-benzazepine. This compound as the hydrobromide has a melting point of 271° (dec.). Substituting 2 trifluoromethyl-3,4-dimethoxytoluene, in Example 2 gives 6-trifluoromethyl-7,8-dimethoxy-1-phenyl-2,3,4,5-tetrahydro-1H-3-benzazepine then hydrolysis with boron tribromide gives 6-trifluoromethyl-7,8-dihydroxy-1-phenyl-3,4,5-tetrahydro-1H-3-benzazepine. This compound as the hydrochloride has a melting point of 155°.

EXAMPLE 11

A mixture of 4.84 g of 50% of sodium hydride in mineral oil and 70 ml of dry dimethylsulfoxide was stirred at 65°–70° for 80 minutes. After dilution with 70 ml of dry tetrahydrofuran, the mixture was cooled to 0° while a solution of 19.0 g (0.093 mole) of trimethylsulfonium iodide in 100 ml of dimethylsulfoxide was added. A solution of 12.6 g (0.0928 mole) of m-anisaldehyde in 40 ml of tetrahydrofuran was quickly added. After stirring for 15 minutes at 0° and 1½ hour at 25°, the mixture is poured into 1½ l. of ice/water slurry and extracted well with water. The combined organic layers were washed with brine, dried and concentrated to give 13 g of crude epoxide. This is mixed with 13.0 g of 2-(2-chloro-3,4-dimethoxyphenyl)ethylamine and heated at 110° for 4 hours. The product was chromatographed over silica gel with 3% methanol/chloroform. The product containing cuts were worked up to given 1.9 g of N-[2-(2-chloro-3,4-dimethoxyphenyl)-ethyl]-2-hydroxy-2-(m-methoxyphenyl)ethylamine, m.p. 95.5°–96.5°.

The p-chlorophenyl congener melted at 99°–100°. The p-methylphenyl congener melted at 117°–118°.

The m-methoxy substituted hydroxyphenethylamine intermediate (1.7 g) in 25 ml of 48% hydrogen bromide solution was cyclized in trifluoroacetic acid-sulfuric acid as described above; 6-chloro-7,8-dimethoxy-1-(m-methoxyphenyl)-2,3,4,5-tetrahydro-1H-3-benzazepine hydrobromide.

The p-chlorophenyl-7,8-dihydroxy congener melted at 243°–246°. The p-methylphenyl-7,8-dihydroxy congener melted at 250°–253°.

EXAMPLE 12

A mixture of 8.0 g of 2-chloro-3,4-dimethoxy-phenethylamine and 5.25 g of m-trifluoromethyl-α-methoxyphenethylbromide is heated at 100°–105° for 2½ hours. The product was partitioned between ethyl acetate and 5% sodium bicarbonate solution. The organic layer was removed, washed with brine, dried and concentrated. The residue was passed over 350 g of silica gel with 1 to 2% methanol/chloroform. The resulting product was an oil whose hydrochloride melted at 200°–202°. The oily base (2.5 g) was heated with 50 ml of 48% hydrogen bromide and worked up as above to give the desired 6-chloro-7,8-dihydroxy-1-(m-trifluoromethylphenyl)-2,3,4,5-tetrahydro-1H-3-benzazepine hydrobromide, m.p. ~250°.

6-Bromo-7,8-dimethoxy-1-phenyl-3-trifluoroacetyl-2,3,4,5-tetrahydro-1H-3-benzazepine (5 g, prepared by reaction of trifluoroacetic anhydride in benzene on the N-hydrogen compound) is reacted with an excess of butyl lithium in ether to give the 6-lithium salt-3-butyllithium adduct. This intermediate is reacted without isolation with iodine. After hydrolysis with water, 6-iodo-7,8-dimethoxy-1-phenyl-,3,4,5-tetrahydro-1H-3-benzazepine is obtained. This compound is treated with boron tribromide as described above to give the 7,8-dihydroxy derivative.

2-Chloro-3-hydroxy-4-methoxybenzaldehyde is treated with hydrogen bromide to give 2-chloro-3,4-dihydroxybenzaldehyde which is converted to the methylenedioxy derivative with dibromomethane as described above. The product is condensed with nitromethane and the resulting nitroethylene reduced to give the phenethylamine. This compound is condensed with p-methoxystyrene oxide to give the α-hydroxyphenethylamine intermediate which is treated with an excess of trifluoroacetic acid at room temperature for 18 hours to give 6-chloro-7,8-methylenedioxy-1-phenyl-2,3,4,5-tetrahydro-1H-3-benzazepine. This compound is split using boron trichloride as described above to give 6-chloro-7,8-dihydroxy-1-p-methoxyphenyl-2,3,4,5-tetrahydro-1H-3-benzazepine.

EXAMPLE 13

A solution of 0.74 g (0.002 mole) of 6-chloro-7,8-dihydroxy-1-phenyl-2,3,4,5-tetrahydro-1H-3-benzazepine hydrochloride, 0.55 g (0.0025 mole) of p-trifluoromethyl benzoylchloride, 0.17 g (0.002 mole) of sodium bicarbonate and 40 ml of 1:1 acetone-water solution was stirred overnight under nitrogen. The mixture was evaporated to dryness. The residue was extracted with ethylacetate. The extracted material was purified over a silica gel column using methanol-ethyl acetate to give 6-chloro-7,8-dihydroxy-1-phenyl-3-(p-trifluoromethylbenzoyl)-2,3,4,5-tetrahydro-1H-3-benzazepine, m.p. 243°–245° (dec.).

This compound (1.65 g, 0.00357 mole) in 120 ml of tetrahydrofuran was added to 15 ml of 1 M boron hydridetetrahydrofuran. After heating at reflux for 2 hours methanol was added with 10 ml of 6 N hydrochloric acid. The solution was evaporated to give a white solid which was dissolved in 50 ml of 6 N hydrochloric acid, heated at reflux for 1 hour and again evaporated. The white solid was purified from methanolethyl acetate-ether to give 6-chloro-7,8-dihydroxy-1-phenyl-3-(p-trifluoromethylbenzyl)-2,3,4,5-tetrahydro-1H-3-benzazepine hydrochloride, m.p. 239°–241° (dec.).

EXAMPLE 14

Using methods described here in the following compounds were prepared:

6-chloro-7,8-dimethoxy-1-phenyl-3-α-thenoyl-2,3,4,5-tetrahydro-1H-3-benzepine, yellow liquid 6-chloro-7,8-dihydroxy-1-phenyl-3-α-thenoyl-2,3,4,5-tetrahydro-1H-3-benzazepine, green solid 6-chloro-7,8-dihydroxy-1-phenyl-3-α-thenyl-2,3,4,5-tetrahydro-1H-benzazepine hydrochloride, m.p. 237°–240°

6-chloro-7,8-dimethoxy-3-α-furoyl-1-phenyl-2,3,4,5-tetrahydro-1H-3-benzazepine, yellow liquid 6-dihydro-7,8-dihydroxy-3-α-furoyl-1-phenyl-2,3,4,5-tetrahydro-1H-3-benzazepine, brown solid 6-chloro-7,8-dihydroxy-3-α-furylmethyl-1-phenyl-2,3,4,5-tetrahydro-1H-3-benzazepine hydrochloride, m.p. 239°–240°

6-chloro-1-(p-chloro-m-hydroxyphenyl)-7,8-dihydroxy-2,3,4,5-tetrahydro-1H-3-benzazepine hydrobromide, m.p. 270°–273°

6-chloro-1-(m,m-dichloro-p-hydroxyphenyl)-7,8-dihydroxy-2,3,4,5-tetrahydro-1H-3-benzazepine hydrobromide, m.p. 290°–292°

6-chloro-1-(m-chlorophenyl)-7,8-dimethoxy-2,3,4,5-tetrahydro-1H-3-benzazepine hydrochloride, m.p.160°–163°

6-chloro-1-(m-chlorophenyl)-7,8-dihydroxy-3-α-furylmethyl-2,3,4,5-tetrahydro-1H-3-benzazepine hydrochloride, m.p. 241°–243°

6-chloro-1-(m-chlorophenyl)-7,8-dihydroxy-2,3,4,5-tetrahydro-1H-3-benzazepine hydrobromide, m.p. 273°–275°

6-chloro-7,8-dimethoxy-1-(m-methylphenyl)-2,3,4,5-tetrahydro-1H-3-benzazepine hydrochloride, m.p. 136°–140°

6-chloro-7,8-dihydroxy-1-(m-methylphenyl)-2,3,4,5-tetrahydro-1H-3-benzazepine hydrobromide, m.p. 120°–123°

6-chloro-7,8-dimethoxy-3-α-furylmethyl-1-(m-methylphenyl)-2,3,4,5-tetrahydro-1H-3-benzazepine hydrochloride, m.p. 235°–237°

6-chloro-7,8-dihydroxy-3-α-furylmethyl-1-(m-methylphenyl)-2,3,4,5-tetrahydro-1H-3-benzazepine hydrochloride, m.p. 262°–265°

6-chloro-7,8-dihydroxy-1-(o-methylphenyl)-2,3,4,5-tetrahydro-1H-3-benzazepine hydrobromide, m.p. 233°–236°

6-chloro-7,8-diacetoxy-1-phenyl-2,3,4,5-tetrahydro-1H-3-benzazepine hydrochloride, m.p. 234°–235°

6-chloro-7,8-dihydroxy1-(m-chloro-p-hydroxyphenyl)-2,3,4,5-tetrahydro-1H-3-benzazepine hydrobromide, m.p. 295°

6-bromo-7,8-diacetoxy-1-(m-methylphenyl)-2,3,4,5-tetrahydro-1H-3-benzazepine hydrobromide, m.p. 224°.

Many of the compounds of the series exist in the salt form as solvates such as hydrates.

EXAMPLE 15

| Ingredients | Mg. per Capsule |
|---|---|
| 6-Chloro-7,8-dihydroxy-1-phenyl-2,3,4,5-tetrahydro-1H-3-benzazepine (as an acid addition salt) | 125 (free base) |
| Magnesium stearate | 2 |
| Lactose | 200 |

The above ingredients are thoroughly mixed and placed into hard gelatin capsules. Such capsules are administered orally to subjects in need of treatment from 2–5 times daily to induce dopaminergic activity.

EXAMPLE 16

| Ingredients | Mg. per Tablet |
|---|---|
| 6-Chloro-7,8-dihydroxy-1-phenyl-2,3,4,5-tetrahydro-1H-3-benzazepine (as an acid addition salt) | 200 (free base) |
| Corn starch | 30 |
| Polyvinyl pyrrolidone | 12 |
| Corn starch | 16 |
| Magnesium stearate | 3 |

The first two ingredients are thoroughly mixed and granulated. The granules obtained are dried, mixed with the remaining corn starch and magnesium stearate, and compressed into scored tablets.

The capsules or tablets thusly prepared are administered orally to an animal or human requiring stimulation of either central or peripheral dopamine receptors within the dose ranges set forth hereinabove. Similarly other compounds of Formula I and the illustrative examples can be formulated in the same manner to give pharmaceutical compositions useful in the methods of this invention based on their chemical characteristics and their relative biological activity using the tests methods outlined.

What is claimed is:

1. A compound of the formula:

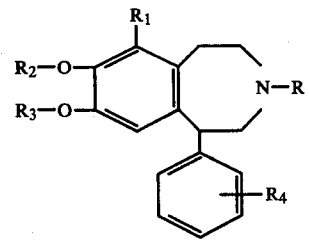

in which:
R is thienylmethyl;
$R_1$ is halo or trifluoromethyl;
$R_2$ and $R_3$ are hydrogen or alkanoyl of from 2–7 carbons; and
$R_4$ is hydrogen or from 1–3 substituents from the group comprising trifluoromethyl, halo, methyl, methoxy or, when another of this group is present, hydroxy or acetoxy;
together with its nontoxic, pharmaceutically acceptable salts.

2. A compound of claim 1 in which $R_4$ is hydrogen.
3. A compound of claim 1 in which $R_1$ is chloro.
4. A compound of claim 1 in which $R_2$ and $R_3$ are hydrogen.
5. The compound of claim 1 being 6-chloro-7,8-dihydroxy-1-phenyl-3-α-thenyl-2,3,4,5-tetrahydro-1H-3-benzazepine hydrochloride.

* * * * *